United States Patent [19]

Carlson

[11] Patent Number: 4,840,182
[45] Date of Patent: Jun. 20, 1989

[54] CONDUCTANCE CATHETER

[75] Inventor: Drew E. Carlson, Providence, R.I.

[73] Assignee: Rhode Island Hospital, Providence, R.I.

[21] Appl. No.: 176,924

[22] Filed: Apr. 4, 1988

[51] Int. Cl.[4] .............................................. A61B 5/02
[52] U.S. Cl. .................................. 128/694; 128/692; 128/734
[58] Field of Search .............................. 128/691–694, 128/713, 734, 419 PG, 419 D, 784–786

[56] References Cited

U.S. PATENT DOCUMENTS

| | | | |
|---|---|---|---|
| 3,882,851 | 5/1975 | Sigworth | 128/693 |
| 4,380,237 | 4/1983 | Newbower | 128/693 |
| 4,641,658 | 2/1987 | Lepper | 128/692 X |
| 4,674,518 | 6/1987 | Salo | 128/695 |

OTHER PUBLICATIONS

Baan, J., et al., "Continuous Stroke Volume and Cardiac Output from Intra-Ventricular Dimensions Obtained with Impedance Catheter", Cardiovasc. Res. 15: 328–334 (1981).
Baan, J., et al., "Continuous Measurement of Left Ventricular Volume in Animals and Humans by Conductance Catheter", Circulation 70: 812–823 (1984).
Burkhoff, D., et al., "Accuracy of Volume Measurement by Conductance Catheter in Isolated, Ejecting Canine Hearts", Circulation 72: 440–447 (1985).
Carlson, Drew E., et al., "Right Atrial Volume During Hemorrhage in the Dog", Am. J. Physiol. H1136–1144 (1986).
McKay, Raymond G., et al., "Instantaneous Measurement of Left and Right Ventricular Stroke Volume and Pressure-Volume Relationships with an Impedance Catheter", Circulation 69: 703–710 (1984).

Primary Examiner—Kyle L. Howell
Assistant Examiner—Angela D. Sykes

[57] ABSTRACT

Conductance catheter apparatus for measuring the volume of a biological chamber, the apparatus including a catheter employing a plurality of electrodes along its length, the plurality including outer transmitting electrodes and intermediate potential sensing electrodes between the outer electrodes, an alternating current source connected to provide alternating currents at high and low frequencies to the outer transmitting electrodes, processing circuitry connected to the intermediate potential sensing electrodes for processing potential signals to obtain conductance signals indicating high frequency and low frequency conductance and for using the conductance signals to determine volume in a manner that excludes parallel conductance through the wall of the chamber and surrounding tissue.

20 Claims, 2 Drawing Sheets

CONDUCTANCE CATHETER

FIELD OF THE INVENTION

The invention relates to measuring the volume of a biological chamber using a conductance catheter.

BACKGROUND OF THE INVENTION

A conductance catheter includes a plurality of electrodes spaced along an elongated portion that is placed in a biological chamber. A current is imposed between the outermost electrodes, and the potentials at the intermediate electrodes are sensed. The conductance of each volume segment between adjacent electrodes is determined by dividing the current by the change in voltage, and the volume of each segment is linearly related to conductance through it. There is a parallel conductance of electricity through the wall of the chamber and the surrounding tissue, and this parallel conductance causes the volume to be overestimated.

Baan, J. et al., "Continuous stroke volume and cardiac output from intraventricular dimensions obtained with impedance catheter," *Cardiovasc, Res.* 15: 328–334, 1981, discloses using a conductance catheter to measure stroke volume by sensing the difference in impedance between the beginning and end of the ejection.

Baan, J., et al., "Continuous measurement of left ventricular volume in animals and humans by conductance catheter," *Circulation* 70: 812–823, 1984 ("Baan et al. 1984"), discloses correcting for parallel conductance by determining an offset correction term, $V_c$, which is determined by either temporarily reducing the volume to zero by suction or by injecting a bolus of cold glucose or hypertonic saline into the chamber, the latter approach also being employed by Burkhoff, D., et al., "Accuracy of volume measurement by conductance catheter evaluated in isolated, ejecting canine hearts", *Circulation*, 72: 440–447, 1985 ("Burkhoff et al. 1985") and Carlson, Drew, E. et al., "Right atrial volume during hemorrhage in the dog," *Am. J. Physiol.*, H1136–H1144, 1986.

Salo U.S. Pat. No. 4,674,518 discloses a conductance catheter using two frequencies at two pairs of drive electrodes having different distances between them. The impedances resulting from different frequencies are plotted to extrapolate the impedance value for infinitely spaced electrodes, and this impedance value is used to determine stroke volume.

McKay, Raymond, G. et al., "Instantaneous measurement of left and right ventricular stroke volume and pressure-volume relationships with an impedance catheter," *Circulation*, 69: 703–710, 1984, discloses using a 1.3 kHz frequency to drive a conductance catheter, owing to the increased resistivity (and thus smaller parallel conductance) of myocardial tissue at 1.3 kHz vis-a-vis resistivity at 20 kHz.

SUMMARY OF THE INVENTION

It has been discovered that the volume of a biological chamber can be accurately measured with a conductance catheter by driving outer electrodes of the catheter at both high and low frequencies, sensing the potentials resulting at intermediate electrodes between the outer electrodes, processing the sensed potentials to obtain conductance values associated with the high frequency and the low frequency, and determining volume based upon the high- and low-frequency conductance values. The parallel conductance through the wall of the biological chamber and surrounding tissue can be excluded from the volume determinations by the solving of simultaneous equations at the two frequencies, owing to a known relationship between the parallel conductances at the two frequencies.

In preferred embodiments, the potentials at adjacent intermediate electrodes are passed through differential amplifiers in order to obtain, for each segment between intermediate electrodes, a signal indicating the difference in potential; the outputs of the differential amplifiers are passed through high-pass and low-pass filters; the outputs of the filters are demodulated and passed through respective dividers to obtain, for each segment, a signal representing the conductance through the segment; and the high-frequency and low-frequency conductances are summed and are combined to determine volume, V(t), according to the following equation:

$$V(t) = K_h[G_h(t) - (G_h(t) - aG_1(t))/(1-ab)]$$

where: $G_h(t)$ and $G_1(t)$ are the summed high and low frequency conductances, and $K_h$, a, and b are empirically determined constants.

Other advantages and features of the invention will be apparent from the following description of a preferred embodiment thereof and from the claims.

DESCRIPTION OF THE PREFERRED EMBODIMENT

The preferred embodiment of the invention will now be described.

Drawings

Structure

Figure 1:
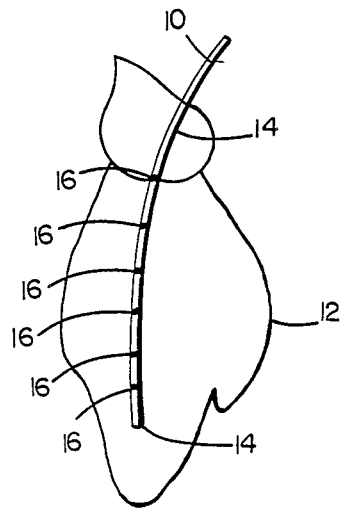
FIG. 1 is a diagrammatic view of a conductance catheter being used to measure the volume of a biological chamber.

Referring to FIG. 1, there is shown conductance catheter 10 placed within biological chamber 12, for example, the left ventricle of a heart. Catheter 10 includes two outer drive electrodes 14 for providing a constant alternating excitation current through the chamber, and six sense electrodes 16 for sensing the resulting potential at locations along catheter 10 within chamber 12.

Figure 2:
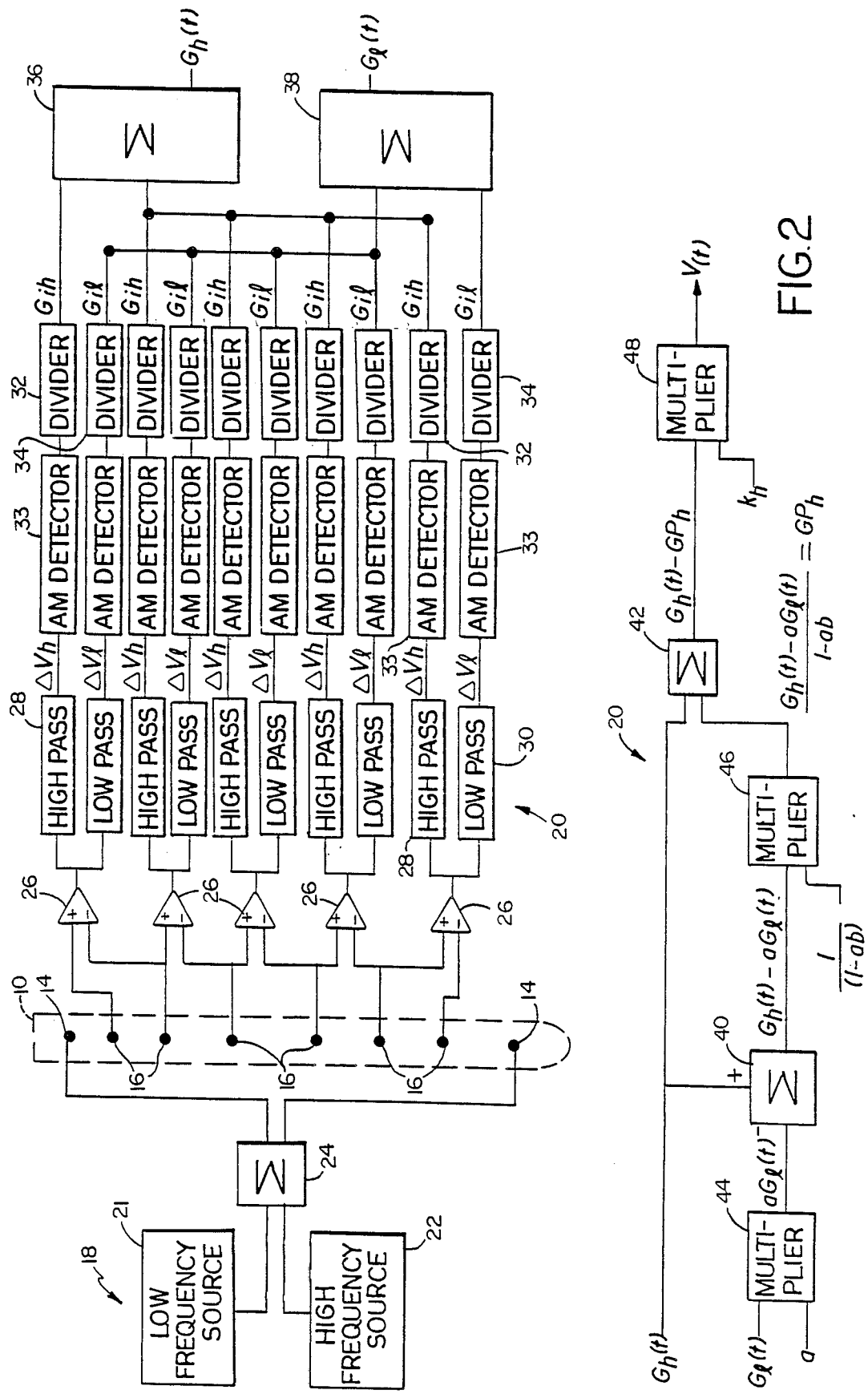
FIG. 2 is a block diagram showing the FIG. 1 catheter connected to low- and high-frequency alternating current sources and signal processing circuitry.

Referring to FIG. 2, catheter 10 is diagrammatically shown electrically connected to its current source circuitry 18 and signal processing circuitry 20. Current source circuitry 18 includes low-frequency source 21, high-frequency source 22, and summing circuit 24, which sums the low- and high-frequency currents and provides them to outer drive electrodes 14. Signal processing circuitry 20 includes five differential amplifiers 26, which are connected to receive as inputs the potentials at respective adjacent pairs of intermediate sense electrodes 16. The difference signal output of each differential amplifier 26 is connected to a high-pass filter 28 and to a low-pass filter 30, which are designed to pass the potential signal components caused by the high-frequency drive signal and the low-frequency drive signal, respectively. The filtered signal outputs of filters 28, 30 are connected via AM detectors 33 to respective dividers 32, 34. The outputs of all dividers 32 (which outputs are conductance signals for segments between intermediate electrodes) are inputted to high-frequency summing circuit 36, and the outputs of all low-frequency dividers 34 are inputted to low-frequency summing circuit 38. The output of summing circuit 36 is directly inputted to summing circuits 40, 42. The output of summing circuit 38 is multiplied at multiplier 44, the output of which is provided to summing circuit 40. The output of summing circuit 40 is multiplied at multiplier 46 and provided as the second input to summing circuit 42. The output of summing circuit 42 is connected to the input of multiplier 48, the output of which is a signal indicating the volume of the chamber. The components of signal processing circuitry 20 are all analog components which provide output signals (voltages) having magnitudes indicating the values of the variables indicated on FIG. 2, as is described in more detail below.

Operation

In operation, high- and low-frequency currents are applied to outer drive electrodes 14, and the potentials at the intermediate sense electrodes 16 are sensed and used by signal processing circuitry 20 to determine volume. Planes of generally equal potential pass through respective intermediate sense electrodes 16, thus breaking the total volume into segments between electrodes, as described in the above-mentioned publications.

Ventricular volume, V(t), can be calculated using equation (1), which was reported by Baan et al. (1984):

$$V(t) = (1/\alpha)*L^2 R_b * \left[ \sum_{i=1}^{5} G_i(t) - GP \right] \quad (1)$$

where:
- $\alpha$ is a dimensionless constant that is generally close to one.
- L is the separation between each pair of sense electrodes.
- $R_b$ is the resistivity of the blood.
- $G_i$ is the conductance of segment i between two sense electrodes and is equal to $I/(V_1 - V_2)$, where I is the current, and $V_1$ and $V_2$ are the potentials at the two electrodes.
- GP is a parallel conductance constant, which has been shown experimentally by Baan et al. (1984) and Burkhoff et al. (1985) to provide a reasonable correction for the conductance of the ventricular wall and the surrounding tissue.

Grouping constants results in equation (2):

$$V(t) = K[G(t) - GP] \quad (2)$$

where:

$$K = L^2 R_b / \alpha \quad (3)$$

$$G(t) = \sum_{i=1}^{5} G_i(t) \quad (4)$$

Equations (5) and (6) describe the calculation of V(t) at low and high frequencies, indicated by subscripts l and h.

$$V(t) = K_h[G_h(t) - GP_h] \quad (5)$$

$$V(t) = K_l[G_l(t) - GP_l] \quad (6)$$

By simultaneously solving equations (5) and (6), the parallel conductance terms can be cancelled out. In particular, because parallel conductance, GP, is constant at a given frequency for a given patient regardless of resistivity of blood, its values at the two frequencies of current through the chamber can be related by a constant ratio:

$$b = GP_l/GP_h \quad (7)$$

Similarly, $K_h$ and $K_l$ can be related by a constant ratio:

$$a = K_l/K_h \quad (8)$$

The simultaneous solution of (5) and (6) yields a value for $$GP_h = [G_h(t) - aG_l(t)]/(1 - ab) \quad (9)$$

that can be used in equation (5) to determine V:

$$V(t) = K_h[G_h(t) - (G_h(t) - aG_l(t))/(1 - ab)] \quad (10)$$

Rearranging equation (10) results in:

$$V(t) = [K_h/(1 - ab)] * [aG_l(t) - abG_h(t)] \quad (11)$$

Referring to FIG. 2, signal processing circuitry 20 employs equation (10) to determine ventricular volume. The voltages provided by adjacent intermediate sense electrodes 16 to differential amplifiers 26 are subtracted at each amplifier 26, and the difference signal output of each amplifier 26 is provided to the respective high-pass filter 28 and low-pass filter 30. The filtered signal outputs of filters 28, 30, $\Delta V_h$ and $\Delta V_l$, are provided to AM detectors 33, which determine the amplitude of each signal. The outputs of AM detectors 33 are provided to respective dividers 32, 34, which provide segment conductance signal outputs $G_{ih}$ and $G_{il}$, having values equal to the current provided between drive electrodes 14 divided by the outputs of detectors 33, the amplitudes of $\Delta V_h$ and $\Delta V_l$, respectively. The $G_{ih}$ signals for adjacent pairs of electrodes 16 are all summed at summing circuit 36, which outputs signal $G_h(t)$, which indicates the total conductance at the high frequency, as in equation (4). Similarly the $G_{il}$ signals for adjacent intermediate electrodes 16 are summed at summing circuit 38, which outputs signal $G_l(t)$, which indicates the total conductance at the low frequency, as in equation 4.

Signals $G_h(t)$ and $G_l(t)$ are combined as indicated in equation (10) by the circuitry shown at the bottom of FIG. 2. Specifically $G_l(t)$ is first multiplied times "a" at multiplier 44, and the resulting signal is then subtracted from $G_h(t)$ at summing circuit 40 to obtain the signal $G_h(t) - aG_l(t)$ (referred to as a first intermediate value). This signal is then multiplied times $1/(1 - ab)$ at multiplier 46, and the resulting output (referred to as a second intermediate value) is added to $G_h(t)$ at summing circuit 42. The output of summing circuit 42 is then multiplied times $K_h$. The output of multiplier 48 is a signal indicating the volume of the chamber. Signal processing circuitry 20 thus provides an analog signal in real time that indicates the volume of biological chamber 12.

The constant "a" can be calculated for each patient using equations (3) and (8) and can be approximated by using a value equal to 1. The constant b can be calculated empirically by determining parallel conductance at the low and high frequencies using the technique of Baan et al. (1984) in which hypertonic saline or glucose solution is injected into the relevant cardiac chamber so that GP is determined at each frequency of excitation. For frequencies of excitation of 1.3 and 20 kHz, the expected values of a and b are about 1 and 0.4, respectively. So long as the high and low frequencies are selected to provide a significant difference in the product of a and b from one, the parallel conductance term can be excluded as described herein.

Other Embodiments

Other embodiments of the invention are within the scope of the following claims. For example, other components or arrangements can be used in signal processing circuitry 20 to obtain high-frequency and low-frequency conductance. Other components or arrangements could be used to determine V(t), e.g., components carrying out equation (11). Also, in place of the analog components of signal processing circuitry 20 shown in FIG. 2, the potentials could be converted to digital signals which are then digitally processed to obtain the volume of the chamber. Also, other methods could be employed to obtain the constants, and the calculations could be carried out in a different manner. Also, although discussion herein is in terms of conductance, the calculations, measurements, and signals could, of course, equivalently be expressed in terms of resistance. Because the invention provides the absolute volume as an output, it is possible to determine ejection fraction, i.e., stroke volume/peak absolute volume.

What is claimed is:

1. Conductance catheter-apparatus for measuring the volume of a biological chamber having a wall, said apparatus comprising
   a catheter employing a plurality of electrodes along its length, said plurality including outer drive electrodes and intermediate potential sensing electrodes between said outer electrodes,
   an alternating current source connected to provide alternating currents at high and low frequencies to said outer drive electrodes, and
   processing means connected to said intermediate potential sensing electrodes for processing potential signals to obtain a high-frequency conductance signal and a low-frequency conductance signal and for using said conductance signals to determine volume in a manner that excludes parallel conductance through the wall of said chamber and surrounding tissue.

2. The apparatus of claim 1 wherein said processing means includes means to determine high-frequency and low-frequency conductance signals for each segment of the chamber between adjacent intermediate electrodes.

3. The apparatus of claim 2 wherein said processing means comprises differential amplifiers connected to receive as inputs the potentials measured at adjacent intermediate electrodes, each said amplifier outputting a difference signal indicating the change in potential between electrodes.

4. The apparatus of claim 3 wherein said processing means also comprises high-pass and low-pass filters connected to receive said difference signals of said differential amplifiers and to output filtered signals.

5. The apparatus of claim 4 wherein there is a said high-pass filter and a said low-pass filter for each said differential amplifier and respective AM detectors that output amplitude signals indicating the amplitudes of said filtered signals.

6. The apparatus of claim 5 wherein said processing means comprises dividers that are each connected to receive a said amplitude signal and to output a segment conductance signal having a magnitude equal to conductance of a respective segment between adjacent electrodes.

7. The apparatus of claim 6 wherein said processing means comprises
   a high-frequency summing circuit that is connected to receive and sum the segment high-frequency conductance signals of said dividers connected to said high-pass filters and to provide said high-frequency conductance signal and
   a low-frequency summing circuit that is connected to receive and sum the segment low-frequency conductance signals of said dividers connected to said low-pass filters and to provide said low-frequency conductance signal.

8. The apparatus of claim 1 wherein said processing means comprises means for subtracting a first constant times said low-frequency conductance signal from said high-frequency conductance signal to obtain a first intermediate value output.

9. The apparatus of claim 8 wherein said processing means comprises means for multiplying said first intermediate value output times a second constant to obtain a second intermediate value output having a value indicating the value of a parallel conductance at one of said high and low frequencies.

10. The apparatus of claim 9 wherein said processing means comprises means for subtracting said second intermediate value output from a said high-frequency conductance signal or low-frequency conductance signal.

11. A method of measuring the volume of a biological chamber having a wall, said method comprising
    placing a catheter employing a plurality of electrodes along its length in said biological chamber, said plurality including outer drive electrodes and intermediate potential sense electrodes between said outer electrodes,
    applying alternating currents at high and low frequencies to said outer drive electrodes,
    processing potential signals provided by said sense electrodes to obtain a high-frequency conductance signal and a low-frequency conductance signal, and
    using said conductance signals to determine volume in a manner that excludes parallel conductance through the wall of said chamber and surrounding tissue.

12. The method of claim 11 wherein said processing includes determining high-frequency and low-frequency conductance signals for each segment of the chamber between adjacent intermediate electrodes.

13. The method of claim 12 wherein said processing comprises providing the potentials measured at adjacent intermediate electrodes as inputs to differential amplifiers, each said amplifier outputting a difference signal indicating the change in potential between electrodes.

14. The method of claim 13 wherein said processing also comprises passing said difference signals through high-pass and low-pass filters and outputting filtered signals.

15. The method of claim 14 wherein there is a said high-pass filter and a said low-pass filter for each said differential amplifier and respective AM detectors that output amplitude signals indicating the amplitudes of said filtered signals.

16. The method of claim 15 wherein said processing comprises providing said amplitude signals to dividers that each output a segment conductance signal having a magnitude equal to conductance of a respective segment between adjacent electrodes.

17. The method of claim 16 wherein said processing comprises summing the segment high-frequency conductance signals of said dividers connected to said high-pass filters to provide said high-frequency conductance signal and summing the segment low-frequency conductance signals of said dividers connected to said low-pass filters to provide said low-frequency conductance signal.

18. The method of claim 11 wherein said using comprises subtracting a first constant times said low-frequency conductance signal from said high-frequency conductance signal to obtain a first intermediate value output.

19. The method of claim 18 wherein said using comprises multiplying said intermediate value output times a second constant to obtain a second intermediate value output having a value indicating the value of a parallel conductance at one of said high and low frequencies.

20. The method of claim 19 wherein said using comprises subtracting said second intermediate value output from a said high-frequency conductance signal or low-frequency conductance signal.

* * * * *